United States Patent
Gianchandani et al.

(10) Patent No.: US 9,440,302 B2
(45) Date of Patent: Sep. 13, 2016

(54) ASSEMBLY AND PLANAR STRUCTURE FOR USE THEREIN WHICH IS EXPANDABLE INTO A 3-D STRUCTURE SUCH AS A STENT AND DEVICE FOR MAKING THE PLANAR STRUCTURE

(75) Inventors: Yogesh B. Gianchandani, Ann Arbor, MI (US); Kenichi Takahata, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 2568 days.

(21) Appl. No.: 10/737,314

(22) Filed: Dec. 16, 2003

(65) Prior Publication Data

US 2004/0149294 A1 Aug. 5, 2004

Related U.S. Application Data

(60) Provisional application No. 60/433,846, filed on Dec. 16, 2002.

(51) Int. Cl.
*A61F 2/06* (2013.01)
*B23H 9/00* (2006.01)
(Continued)

(52) U.S. Cl.
CPC ............. *B23H 9/00* (2013.01); *A61F 2/844* (2013.01); *A61F 2/88* (2013.01); *A61F 2/89* (2013.01); *A61F 2/91* (2013.01)

(58) Field of Classification Search
CPC ............ A61F 5/844; A61F 2/86; A61F 2/88; A61F 2/89
USPC .......................... 623/1.15, 1.16, 1.18, 23.624
See application file for complete search history.

(56) References Cited

U.S. PATENT DOCUMENTS 5,591,230 A * 1/1997 Horn et al. ............... 623/1.17
6,015,387 A   1/2000 Schwartz et al.
(Continued)

FOREIGN PATENT DOCUMENTS

WO    WO 9953862 A1 * 10/1999

OTHER PUBLICATIONS

International Search Report for PCT/US2005/19819, mailed Sep. 6, 2006.

(Continued)

*Primary Examiner* — Diane Yabut
(74) *Attorney, Agent, or Firm* — Marshall, Gerstein & Borun LLP (57) ABSTRACT

An assembly and planar structure for use therein which is expandable into a 3-D structure such as a stent and device for making the planar structure are provided. The planar structure permits the use of planar batch manufacturing technologies to fabricate coronary artery stents. Stents with different wall patterns are fabricated from 50 μm thick stainless steel foil using micro-electro-discharge machining, and expanded to tubular shapes by using angioplasty balloons. The stents are free-standing. The free-standing stents exhibit diameter variations of <±4%, almost zero radial recoil after deflation of the balloon, and longitudinal shrinkage of <3% upon expansion. A variation of the stents uses breakable links to provide additional customization of electrical and mechanical properties. Loading tests reveal that the radial strengths match commercially available stents, while longitudinal compliance, at 0.02 m/N for a 4 mm long section of the stent, is substantially higher.

37 Claims, 6 Drawing Sheets

(51) Int. Cl.
*A61F 2/844* (2013.01)
*A61F 2/88* (2006.01)
*A61F 2/89* (2013.01)
*A61F 2/91* (2013.01)

(56) References Cited

U.S. PATENT DOCUMENTS

| | | | |
|---|---|---|---|
| 6,053,873 | A | 4/2000 | Govari et al. |
| 6,086,604 | A * | 7/2000 | Fischell et al. ............... 606/198 |
| 6,206,835 | B1 | 3/2001 | Spillman, Jr. et al. |
| 6,206,914 | B1 | 3/2001 | Soykan et al. |
| 6,231,516 | B1 | 5/2001 | Keilman et al. |
| 6,278,379 | B1 | 8/2001 | Allen et al. |
| 6,442,413 | B1 | 8/2002 | Silver |
| 6,471,719 | B1 * | 10/2002 | Voinov et al. ............... 623/1.12 |
| 6,586,699 | B1 | 7/2003 | Gianchandani et al. |
| 6,592,518 | B2 | 7/2003 | Denker et al. |
| 6,624,377 | B2 | 9/2003 | Gianchandani et al. |
| 6,729,336 | B2 * | 5/2004 | Da Silva et al. ............. 128/897 |
| 6,802,857 | B1 | 10/2004 | Walsh et al. |
| 6,926,670 | B2 | 8/2005 | Rich et al. |
| 2002/0156525 | A1 * | 10/2002 | Smith et al. ................. 623/1.22 |
| 2002/0173839 | A1 * | 11/2002 | Leopold et al. ............. 623/1.15 |
| 2002/0179573 | A1 | 12/2002 | Gianchandani et al. |
| 2002/0188345 | A1 * | 12/2002 | Pacetti ......................... 623/1.15 |
| 2004/0149294 | A1 | 8/2004 | Gianchandani et al. |
| 2006/0265049 | A1 | 11/2006 | Gray et al. |
| 2007/0213809 | A1 | 9/2007 | Weber |

OTHER PUBLICATIONS

Written Opinion of the International Searching Authority for PCT/US2005/19819, mailed Sep. 6, 2006.
Leung, Dr. Daniel, A., et al., Selection of Stents for Treating Iliac Arterial Occlusive Disease, J. Vasc. Interv. Radiol., vol. 14, No. 2, Feb. 2003, pp. 137-152.
Andersen, P.E., Cartoid Artery Stenting, J. Intrv. Radiol. vol. 13, No. 3, 1998, Abstract.
Rees, C.R. , Stents for, Atherosclerotic Renovascular Disease, J. Vasc. Interv. Radiol., vol. 10, No. 6, 1999, Abstract.
Mueller, Pena C., Metallic Stents in the Biliary Tree, Min. Invas. Ther. & Allied Technol., vol. 8, No. 3, 1999, Abstract.
Auge, B.K., Ureteral Stents and Their Use in Endourology, Curr. Opin. Urol., vol. 12, No. 3, 2002, Abstract.
Kathuria, Y. P., Laser Microprocessing of Stent for Medical Therapy, Proc. IEEE Micromech. Human Sci., Japan, Apr. 1998, pp. 111-114.
Takahata, Kenichi, et al., Batch Mode Micro-Electro-Discharge Machining, Journal of Microelectromechanical Systems, Journal of Microelectromechanical Systems, vol. 11, No. 2, Apr. 2002, pp. 102-110.
Takahata, Kenichi, et al., Coronary Artery Stents Microfabricated From Planar Metal Foil: design, Fabrication, and Mechanical Testing, Proce. IEEE MEMS, 2003, pp. 462-465.
Conti, JC, et al., The Durability of Silicone Versus Latex Mock Arteries, Proc. ISA Biomed, Sci. Instrum. Symp, vol. 37, 2001, pp. 305-312.
Chua, S.N. David, et al., Finite-Element Simulation of Stent Expansion, Journal of Materials Processing Technology, vol. 120, 2002, pp. 335-340.
Flueckiger MD, Fritz, et al., Strength, Elasticity, and Plasticity of Expandable Metal Stents: In Vitro Studies with Three Types of Stress, J. Vasc. Interv. Radiol., vol. 5, No. 5, 1994, pp. 745-750.
Rieu, Regis, et al., Radial Force of Coronary Stents: A Comparative Analysis, Catheter. Cardiovasc. Interv., vol. 46, 1999, pp. 380-391.
Akin, Tayfun et al. "RF Telemetry Powering and Control of Hermetically Sealed Integrated Sensors and Actuators," Center for Integrated Sensors and Circuits, Dept. of Electrical Engineering and Computer Science, University of Michigan, IEEE, 1980, pp. 145-148.
Miao, Chih-Lei et al. "Body Position and Pressure Distribution Sensors in Prosthetic Systems for Computer-Controlled Walking," Proc. 4th Int. Conf. Solid-State Sensor and Actuators (1987), pp. 57-60.
Shoji, Shuichi et al. "Fabrication of an Impantable Capacitive Type Pressure Sensor," Dept. of Electronic Engineering, Tohoku University, Sendai 980, Japan, Proc. 4th Int. Conf. Solid-State Sensor and Actuators (1987) pp. 305-308.
Spillman, Jr., William B. "Sensing and Processing for Smart Structures," Proceedings of the IEEE, vol. 84, No. 1, Jan. 1996, pp. 68-77.
Ziaie, Babak et al. "A High-Current IrOx Thin-Film Neuromuscular Microstimulator," Center for Integrated Sensors and Circuits, Dept. of Electrical Engineering and Computer Science, University of Michigan, IEEE, 1991, pp. 124-127.
Akar et al., "A wireless batch sealed absolute capacitive pressure sensor," Sensors and Actuators A, 95, pp. 29-38 (2001).
DeHennis et al., "A double-sided single-chip wireless pressure sensor," Proc. IEEE MEMS 2002, pp. 252-255 (2002).
E. Park et al., "Hermetically Sealed Inductor-Capacitor (LC) Resonator for Remote Pressure Monitoring," Jpn. J. Appl. Phys., vol. 37, pp. 7124-7128 (1998).

* cited by examiner

ASSEMBLY AND PLANAR STRUCTURE FOR USE THEREIN WHICH IS EXPANDABLE INTO A 3-D STRUCTURE SUCH AS A STENT AND DEVICE FOR MAKING THE PLANAR STRUCTURE

CROSS-REFERENCE TO RELATED APPLICATION

This application claims the benefit of U.S. provisional application Ser. No. 60/433,846, filed Dec. 16, 2002 and entitled "Design and Fabrication of Stents Using Planar Metal Foils."

STATEMENT REGARDING FEDERALLY SPONSORED RESEARCH OR DEVELOPMENT

This invention was made with Government support under National Science Foundation Grant No. ECS-0233174. The Government has certain rights in the invention.

BACKGROUND OF THE INVENTION

1. Field of the Invention

This invention relates to assemblies and planar structures for use therein which are expandable into 3-D structures such as stents and devices for making the planar structures.

2. Background Art

The following references are noted hereinbelow:
[1] D. A. Leung et al., "Selection of Stents for Treating Iliac Arterial Occlusive Disease," J. VASC. INTERV. RADIOL., Vol. 14, 2003, pp. 137-52.
[2] P. E. Andersen et al., "Carotid Artery Stenting," J. INTERV. RADIOL., Vol. 13, No. 3, 1998, pp. 71-6.
[3] C. R. Rees, "Stents for Atherosclerotic Renovascular Disease," J. VASC. INTERV. RADIOL., Vol. 10, No. 6, 1999, pp. 689-705.
[4] C. Pena et al., "Metallic Stents in the Biliary Tree," MIN. INVAS. THER. & ALLIED TECHNOL., Vol. 8, No. 3, 1999, pp. 191-6.
[5] B. K. Auge et al., "Ureteral Stents and Their Use in Endourology," CURR. OPIN. UROL., Vol. 12, No. 3, 2002, pp. 217-22.
[6] Y. P. Kathuria, "Laser Microprocessing of Stent for Medical Therapy," PROC. IEEE MICROMECH. HUMAN SCI., 1998, pp. 111-14.
[7] K. Takahata et al., "Batch Mode Micro-Electro-Discharge Machining," IEEE J. MICROELECTROMECH. SYS., Vol. 11, No. 2, 2002, pp. 102-10.
[8] K. Takahata et al., "Coronary Artery Stents Microfabricated from Planar Metal Foil: Design, Fabrication, and Mechanical Testing," PROC. IEEE MEMS, 2003, pp. 462-5.
[9] J. C. Conti et al., "The Durability of Silicone Versus Latex Mock Arteries," PROC. ISA BIOMED. SCI. INSTRUM. SYMP., Vol. 37, 2001, pp. 305-12.
[10] R. C. Hibberler, "Mechanics of Materials Third Edition." PRENTICE-HALL, INC., 1997.
[11] S. N. David Chua et al., "Finite-Element Simulation of Stent Expansion," J. MATERIALS PROCESSING TECHNOL., Vol. 120, 2002, pp. 335-40.
[12]. "Metals Handbook Ninth Edition," Vol. 8 Mechanical Testing, AMERICAN SOCIETY FOR METALS, 1985.
[13] F. Flueckiger et al., "Strength, Elasticity, and Plasticity of Expandable Metal Stents: In-Vitro Studies with Three Types of Stress," J. VASC. INTERV. RADIOL., Vol. 5, No. 5, 1994, pp. 745-50.
[14] R. Rieu et al., "Radial Force of Coronary Stents: A Comparative Analysis," CATHETER. CARDIOVASC. INTERV., Vol. 46, 1999, pp. 380-91.
[15] For example: J. D. Lubahn et al., "Plasticity and Creep of Metals," JOHN WILEY & SONS, 1961.

U.S. Pat. Nos. 6,624,377 and 6,586,699 are related to the present application.

Stents are mechanical devices that are chronically implanted into arteries in order to physically expand and scaffold blood vessels that have been narrowed by plaque accumulation. Although they have found the greatest use in fighting coronary artery disease, stents are also used in blood vessels and ducts in other parts of the body. These include iliac arteries [1], carotid arteries [2], renal arteries [3], biliary ducts [4] and ureters [5]. The vast majority of coronary stents are made by laser machining of stainless steel tubes [6], creating mesh-like walls that allow the tube to be expanded radially with a balloon that is inflated during the medical procedure, known as balloon angioplasty. This fabrication approach offers limited throughput and prevents the use of substantial resources available for fabricating planar microstructures.

Micro-electro-discharge machining (µEDM) is another option for cutting metal microstructures. This technique is capable of performing 3-D micromachining in any electrical conductor with sub-micron tolerance and surface smoothness. It has not been extensively used for stent production in the past because traditional µEDM that uses single electrodes with single pulse timing circuits often suffers from even lower throughput than the laser machining. However, it has been recently demonstrated that the throughput of µEDM can be vastly increased by using spatial and temporal parallelism, i.e., lithographically formed arrays of planar electrodes with simultaneous discharges generated at individual electrodes [7].

SUMMARY OF THE INVENTION

An object of the present invention is to provide an assembly and planar structure for use therein which is expandable into a 3-D structure such as a stent and device for making the planar structure wherein the planar structure can be readily manufactured.

In carrying out the above object and other objects of the present invention, a planar structure expandable into a 3-D structure is provided. The planar structure includes first and second spaced side beams which extend along a longitudinal axis. A plurality of spaced cross-bands connect the side beams together. A first set of the cross-bands are expandable in a first direction substantially perpendicular to the longitudinal axis to form a 3-D structure.

The side beams may be substantially straight and/or continuous.

A second set of the cross-bands may be expandable in a second direction substantially opposite the first direction to form a mesh-like 3-D structure.

Adjacent cross-bands may be expandable in the opposite directions to form a mesh-like 3-D structure.

The planar structure may plastically deform during expansion so that the 3-D structure is free-standing, or may have a cylindrical geometry.

The 3-D structure may be a tubular stent.

The planar structure may include a conductive foil.

Each of the cross-bands may include a series of folded beams.

The folded beams may have an involute pattern or a switchback pattern.

Each of the cross-bands may include hinges for interconnecting adjacent folded beams.

The side beams and cross-bands may include biocompatible surface coatings.

The side beams and cross-bands may be made of a biocompatible metal.

The cross-bands may be made of a shape-memory alloy, and the planar structure may be self-expandable.

The side beams and cross-bands may be made of at least one of a biocompatible and a biodegradable polymer.

The side beams and cross-bands may be formed by removing material from a sheet of material.

The sheet of material may include conductive foil, and the side beams and cross-bands may be formed by electric discharge machining the conductive foil.

At least the first side beam may include a link portion having a mechanical strength lower than other portions of the first side beam to allow the first side beam to break at the link portion during expansion of the first set of cross-bands.

The link portion may be thinned relative to the other portions of the first side beam.

The link portion may be made of a fragile material relative to the other portions of the first side beam.

The 3-D structure may be a helical coil.

The helical coil may include at least one electrical inductor.

The 3-D structure may comprise at least one electrical conductor.

The helical coil may include first and second spaced rings at opposite ends thereof. Each of the rings may be formed by an adjacent pair of expanded cross-bands.

At least the first ring may include a dielectric part which mechanically connects but electrically insulates adjacent portions of the first ring.

At least the first ring may include a link portion having a mechanical strength lower than other portions of the first ring to allow the first ring to break at the link portion during expansion of the first set of cross-bands to open an electrical path formed by the first ring.

At least one of the side beams and the cross-bands may include a dielectric part which mechanically connects but electrically insulates adjacent portions of the at least one of the side beams and the cross-bands.

Further in carrying out the above object and other objects of the present invention, an assembly including a planar structure is provided. The planar structure includes a pair of spaced side beams which extend along a longitudinal axis. First and second sets of spaced cross-bands connect the side beams together. A balloon is mounted on the cross-bands so that adjacent cross-bands are disposed on opposite first and second sides of the balloon. Inflation of the balloon causes the first set of cross-bands on the first side of the balloon to expand in a first direction and the second set of cross-bands on the second side of the balloon to expand in a second direction substantially opposite the first direction and substantially perpendicular to the longitudinal axis to form a mesh-like, 3-D structure.

The balloon may be an angioplasty balloon and the 3-D structure may be a tubular stent.

The assembly may further include a catheter tube in fluid communication with the angioplasty balloon.

Still further in carrying out the above object and other objects of the present invention, a device for use in a electric discharge machining system to form an expandable planar structure from a conductive planar workpiece is provided. The device includes a substrate and a planar electrode formed on the substrate. The planar electrode includes a pair of spaced, side electrode members extending along a longitudinal axis to form a pair of side beams of the structure from the workpiece. The planar electrode further includes a plurality of spaced cross-band electrode members to form a plurality of spaced cross-bands of the structure from the workpiece. The cross-bands connect the side beams together.

The side electrode members and the cross-band electrode members may include a plurality of copper structures formed by electroplating the substrate.

The substrate may include a semiconductor wafer. The side electrode members and the cross-band electrode members may include a plurality of semiconductor structures formed by removing material from the semiconductor wafer.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 5 is a schematic view of an electric discharge machining system including an electrode for cutting the planar structure of FIG. 1a;

FIG. 6 is a perspective schematic view of the system of FIG. 5 with a device including a planar electrode formed on a substrate for cutting a workpiece to form the planar structure of FIG. 1a;

FIG. 7b is a close-up view of a thinned link of a side beam of the planar structure of FIG. 7a;

FIG. 8b is a close-up view of a fragile plug embedded in a side beam of the planar structure of FIG. 8a;

FIG. 10b is a simplified view of a 3-D structure in the form of a pair of helical inductors formed after the expansion of the planar structure of FIG. 10a;

FIG. 11a is a perspective, simplified view of an expanded 3-D structure having end rings;

FIG. 11b is a close-up view of plugs of a dielectric material embedded in the end rings of FIG. 11a;

FIG. 12a is a perspective, simplified view of an expanded 3-D structure having end rings;

FIG. 12b is a close-up view of breakable links or portions of the end rings of FIG. 12a;

FIG. 13b is a close-up view of an interconnecting dielectric plug used in the planar structure of FIG. 13a.

DETAILED DESCRIPTION OF THE PREFERRED EMBODIMENTS

A new assembly and planar structure for use therein which is expandable into a 3-D structure such as a stent and device for making the planar structure are disclosed herein. Also, this invention presents a new approach to the design and manufacture of coronary artery stents, which permits the use of planar batch fabrication techniques using microelectrodischarge machining. The devices are compatible with standard stenting tools and procedures. The wall patterns were designed so that both stress relief and the mechanical strength are simultaneously achieved in the expansion.

Figure 1A:
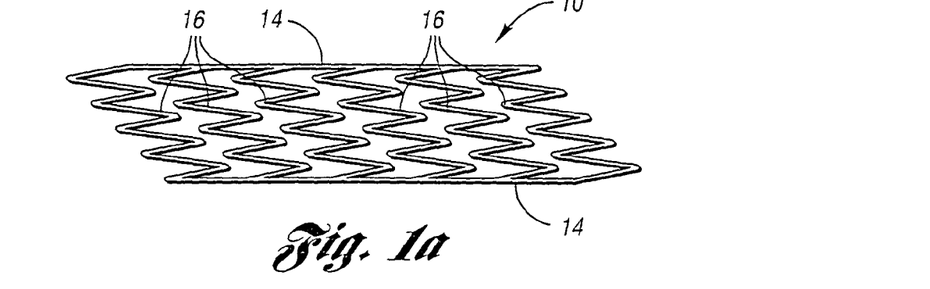
FIGS. 1a-1c are generalized, schematic views of a planar structure or stent of the present invention, mounted on a deflated balloon and expanded to a cylindrical geometry, respectively.
Figure 1B:
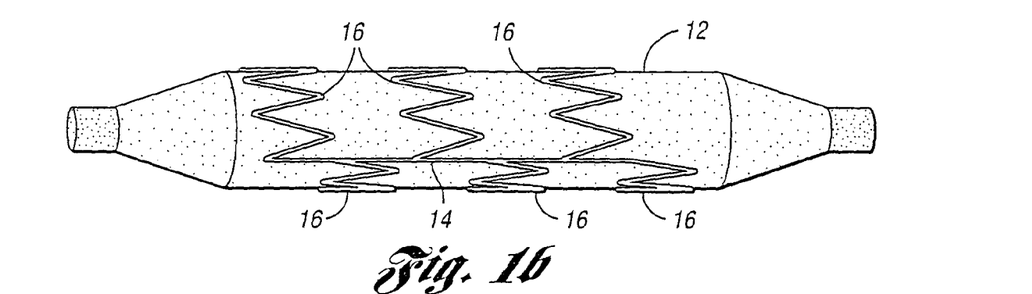
Figure 1C:
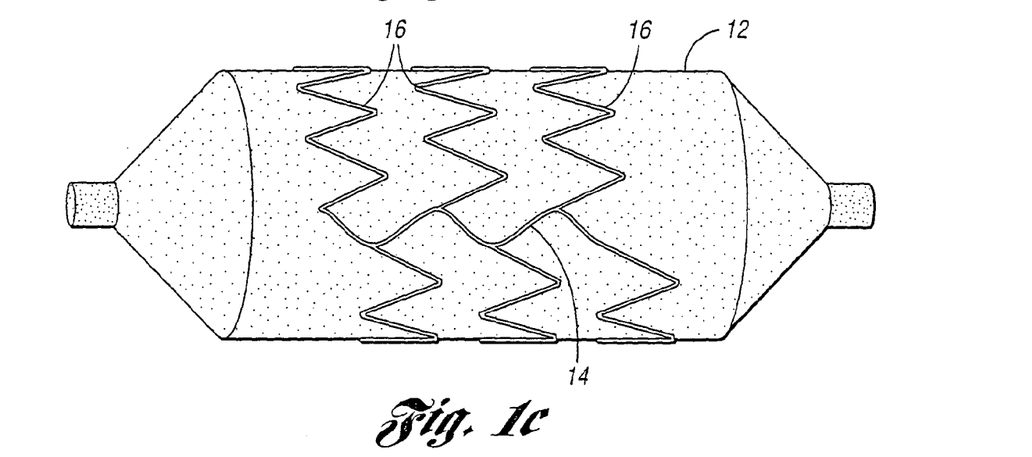

Referring to FIGS. 1a-1c, a generalized schematic view of a stent or planar structure constructed in accordance with the present invention is generally indicated at 10. The stent 10 is mounted on a deflated balloon 12 in FIG. 1b and on the balloon 12 when inflated in FIG. 1c. The stent 10 includes involute bands 16 tied between a pair of side beams 14. Measurements demonstrate that the designs have the same radial strength as a commercial stent even though the former use metal that is only about half as thick. The thinner walls also contributed to achieving higher longitudinal flexibility than a commercial one in the expanded state. Both the radial strength and the flexibility are found to have no significant dependence on orientation relative to the original planar direction of the foil. Dimensional variations in tubular diameter, longitudinal shrinkage, and radial recoiling in the expanded stents are at most a few percent.

The invention will also facilitate other three-dimensional structures such as antennas and transformers. Using this approach, any electrically conductive material can be used to form a tubular mesh-like structure. This includes structures which have attached elements that do not conform to the shape of the cross-section of the tube, such as tangential cantilever or loop attached to the perimeter. The structures can be used as inductors (i.e., FIG. 10b), antennas, transformers, or capacitors for electrical circuits. They may also be used for mechanical functions such as springs, trusses, etc. in microsystems.

The new fabrication approach uses metal foils as starting materials for the stents 10, which permits the parallelism described in U.S. Pat. Nos. 6,624,377 and 6,586,699 to be exploited, thereby offering high throughput and repeatability. The favored mechanical characteristics including radial strength and longitudinal compliance in expanded stents (i.e., FIG. 1c) have been experimentally and theoretically investigated, and are discussed with comparisons to commercial stents.

A variation that uses strategically located breakable links (FIGS. 7a, 8a, 9a, 10a) in the stent provides additional freedom in customizing the mechanical and electrical properties of these devices.

Design and Fabrication

Figure 2:
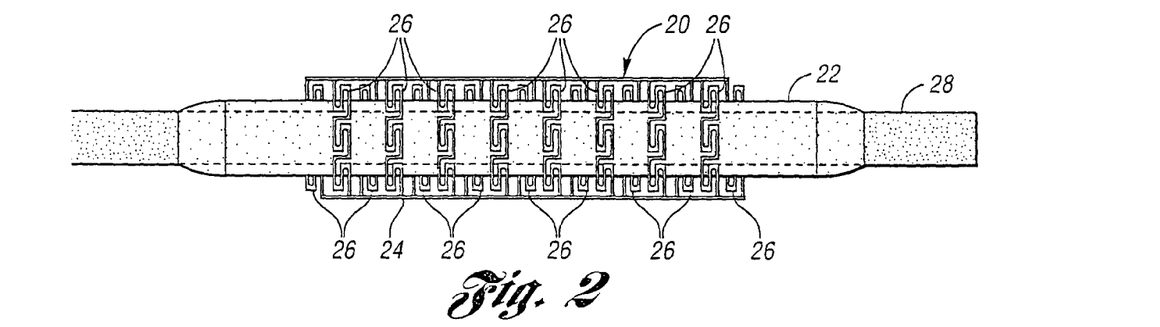
FIG. 2 is a detailed schematic view of a first embodiment (i.e., design) of a planar structure of FIG. 3 mounted on a deflated angioplasty balloon in fluid communication with a catheter tube.

The fabrication approach was applied to μEDM 50 μm-thick stainless steel foil into a planar structure, generally indicated at 20, that could be slipped over an angioplasty balloon 22 and be reshaped into a cylinder when deployed in the manner of a conventional stent via a catheter tube 28, as shown in FIG. 2. The planar pattern of the structure 20 provides the important mechanical characteristics of radial stiffness and longitudinal compliance in the expanded structure. In order to reduce the likelihood of joint failure, it was decided to develop a structure 20 that was completely flexural in nature, and did not have any bonded or hinged joints. This effort used 50 μm-thick type 304 steel which is very similar to the 316 steel commonly used for commercially available stents.

Figure 14:
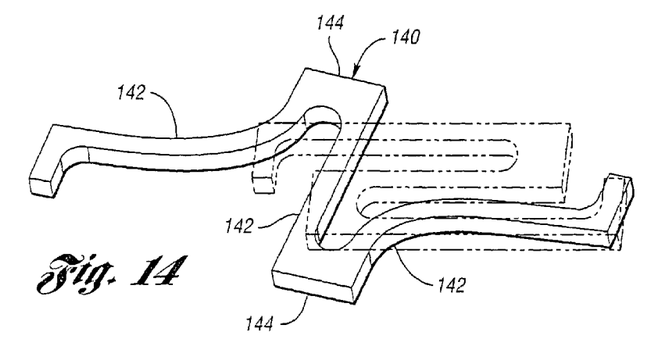
FIG. 14 is a perspective, schematic view of folded beams having an involute shape in initial (indicated by dashed lines) and expanded (indicated by solid lines) positions.

Several layouts were designed and experimentally tested. The best results in terms of mechanical characteristics (discussed herein below) were obtained with the design shown in FIGS. 2 and 3, which is referred to as design 1 (i.e., units are in μm). The pattern has two longitudinal side beams 24, which are connected transversely by cross-bands 26, each of which contain three identical involute loops (i.e., FIG. 14 shows one such loop). The involute shape is tailored to provide selected stress-relief during expansion of the stent 20 to the desired deployment diameter, which is 2.65 mm in this case. In order to increase radial strength, this design uses a larger number of cross-bands 26 per unit length of the stent 20 and beams $A_n$, $C_n$, and $E_n$ are designed to be longer than the others, $B_n$ and $D_n$.

Figure 4:
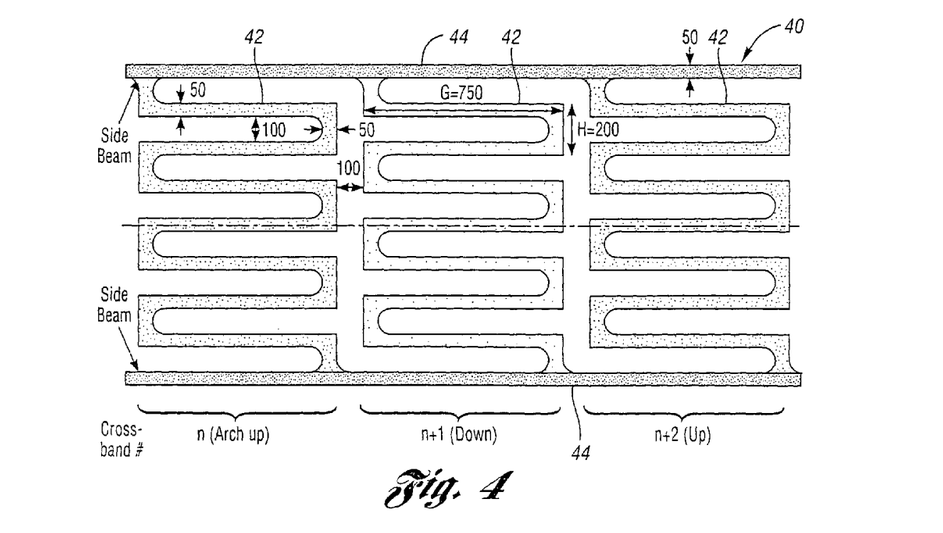
FIG. 4 is a top plan schematic view of a second embodiment of the planar structure having a pattern of folded beams in a switchback shape.

Another representative planar substrate is illustrated at 40 in FIG. 4 (i.e., units again in μm), which is referred to as design 2. It has similar dimensions and a configuration that uses an array of cross-bands 42 and two side beams 44, but the cross-bands 42 have a switchback pattern in this case. In contrast to the involute design, the beams in segment G, which are parallel to the longitudinal axis, are longer than the others in segment H, which are perpendicular to the axis. This design, in general, has a higher expansion ratio to the initial width between the side beams 44 in radial direction, but fewer cross-bands 42 along the longitudinal axis.

To emulate the deployment of a stent, the angioplasty balloon 22 was threaded through the 7 mm-long planar structure 20, as shown in FIG. 2, such that the transverse bands 26 alternated above and below it. With the set-up illustrated in FIGS. 1b and 2, the stent 20 was expanded by inflating the balloon 22 with liquid up to 12 atm. pressure, in a manner identical to commercial stents, resulting in the structure similar to the one shown in FIG. 1c. Variation in the diameter of expanded stents was typically within ±4%, while radial recoil upon deflation of the balloon 22 was even smaller than that. The shrinkage in length upon the expansion was <3%. A deployment inside a mock artery was done. The mock artery used was a commercially available silicone-based tube (Dynatek Dalta Scientific Instruments, MO, USA) with 3 mm diameter and 0.25 mm wall thickness, which is tailored to have radial compliance comparable to human coronary arteries [9]. In this deployment, the stent 20 was expanded to 3.5 mm diameter. The tube had a distended sidewall at the location where the stent 20 was deployed, demonstrating mechanical strength large enough to prevent the relaxation of the simulated artery.

Upon expansion of the stent, beams in the structure are permanently deformed as shown in FIG. 14. The pattern of the stent must, therefore, be designed to accommodate large deformations so that the maximum tensile stress is less than the ultimate stress, which is about 517 MPA for the 304 stainless steel [10]. The deformation and resultant stresses were evaluated by using an FEA package, ANSYS™. The simulation used a bilinear stress-strain model, and the following mechanical properties of the steel [10,11]: Young's modulus=193 GPA, yield stress=207 MPA, tangent modulus=692 MPA, and Poisson's ratio=0.27. FIG. 14 shows a unit involute section, generally indicated at 140, of the cross-bands of design 1 with a displacement that approximately corresponds to the deployed diameter. The section 140 includes beams 142 with interconnecting hinges 144. The maximum von Mises stress appears at the location indicated near the flexural hinge element $B_n$ and is 382 MPA, sufficiently below the ultimate stress.

Figure 3:
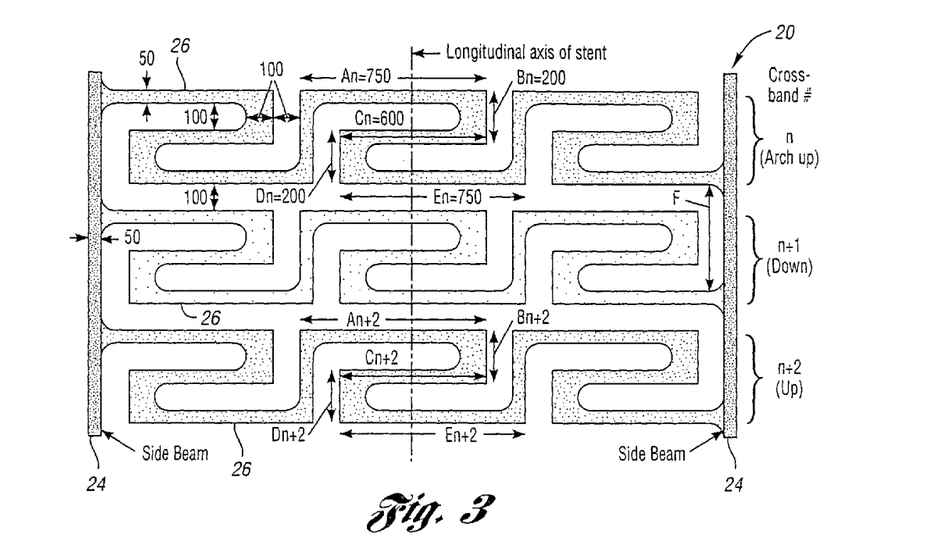
FIG. 3 is a top plan schematic view of the first embodiment of the planar structure having a pattern of folded beams in an involute shape.

In addition to the bending of beam segments, torsional deformations also play important roles in expanding a stent and maintaining its final shape. The most significant ones are in the side beams 24, which are twisted by 90-180° along the segment F (labeled in FIG. 3) between two adjacent bands 26. Different torsional deformation was observed at a flexural hinge H in design 2 (i.e., FIG. 4). The approximate shear strain for both these cases was shown on a shear stress versus shear strain response curve for 304L stainless steel obtained from [12]. It was evident that beam fracture associated with only the torsion is not a concern for the stent. For the test, the hinge as well as the beams had 50 µm square cross-section. Although the strain due to this torsion is well below the fracture point, additional deformations at the site also include bending that may further increase the maximum strain experienced. Mechanical failure was observed due to a combination of severe bending and tension. This fracture was observed in design $1_A$, a precursor to design 1 for which width of flexural hinges was 50 µm, and segments $A_n$, (and $E_n$), $B_n$ (and $D_n$), and $C_n$ were 550, 150, and 450 µm, respectively. The narrower width and shorter length in the flexural hinges, $B_n$ and $D_n$ of this design contributed increasing the tensile stress at the hinge. Since this was the only failure experienced, it is likely that an instance of metallurgical defect may have contributed to it. In design 1, a larger safety margin was incorporated by two changes: (i) doubling the widths of the segments $B_n$ and $D_n$ from 50 µm to 100 µm, and (ii) increasing the lengths of the same segments from 150 µm to 200 µm by doubling the gap between adjacent beams, as seen in FIG. 3.

Figure 7A:
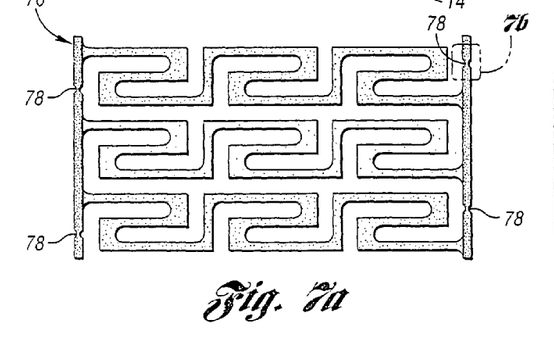
FIG. 7a is a top plan schematic view of an embodiment of the planar structure.
Figure 7B:
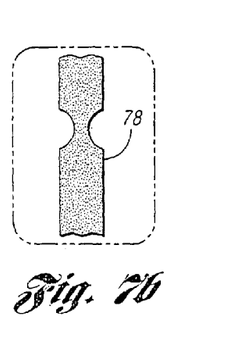
Figure 8A:
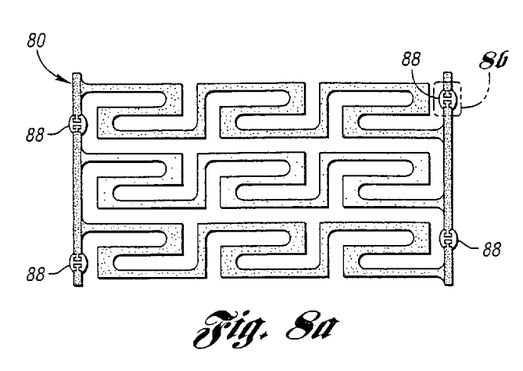
FIG. 8a is a top plan schematic view of another embodiment of the planar structure.
Figure 8B:
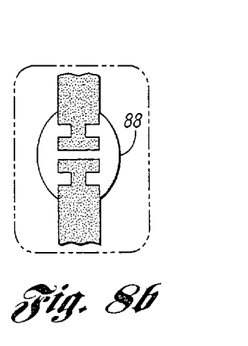
Figures 9A, 9B:
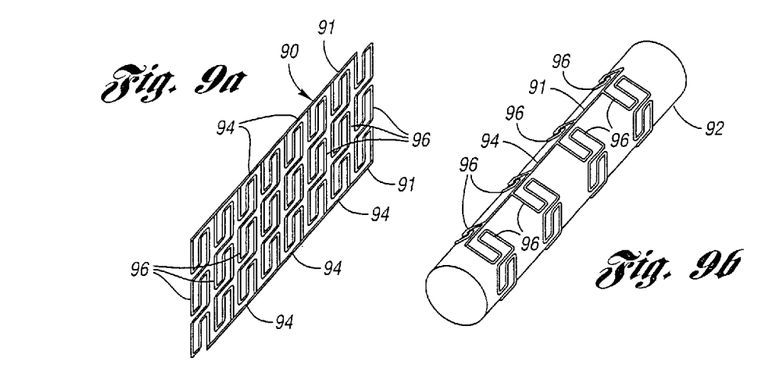
FIGS. 9a-9d are perspective, schematic views showing a planar structure having breakable links by itself, on a deflated balloon, on a fully expanded balloon, and its electrical path equivalent to the final stage of FIG. 9c, respectively, wherein the resulting 3-D structure includes a helical coil with end rings.
Figures 9C, 9D:
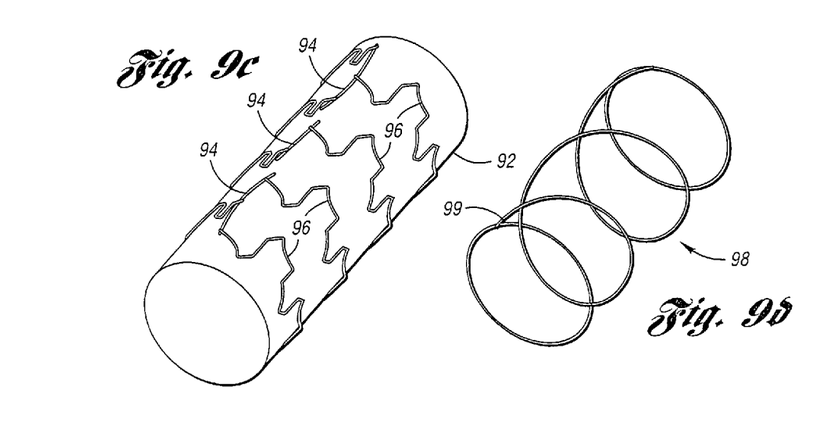
Figure 10A:
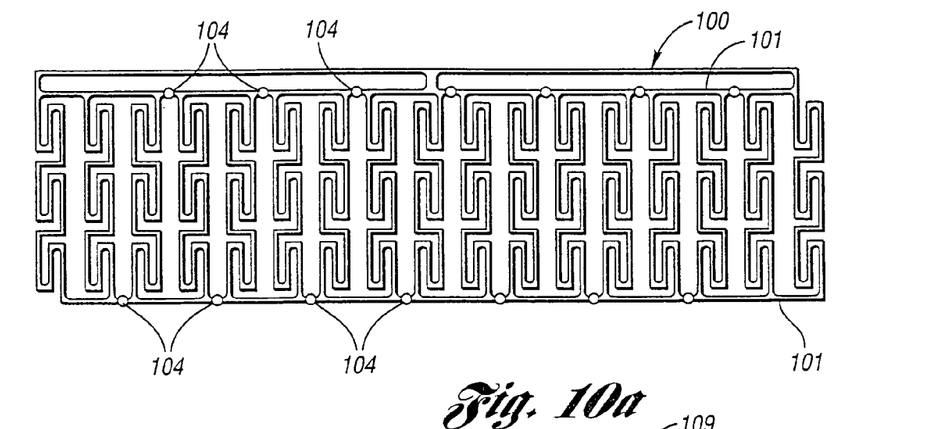
FIG. 10a is a top plan schematic view of another planar structure having breakable links.
Figure 10B:
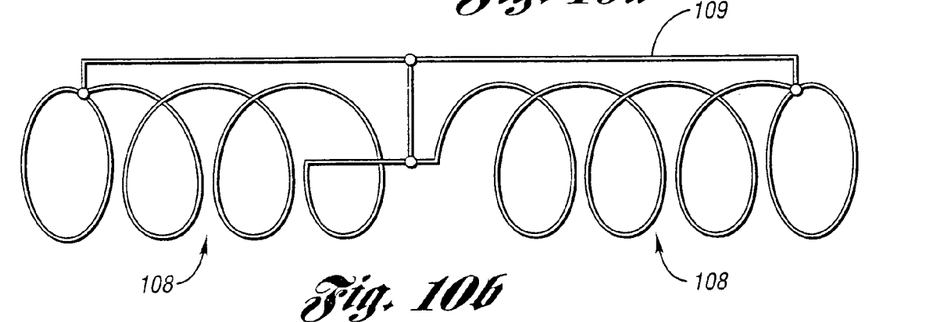

In addition to the stent fabrication, the planar scheme can be easily extended to fabrication of 3-D inductors, generally indicated at 108 in FIG. 10b. The final 3-D structure is essentially a set of series-connected rings which offer negligible inductance. Use of breakable links in planar structures 70, 80, 90 and 100 (FIGS. 7a, 8a, 9a, and 10a) permits formation of helical coils or inductors 98 and 108 (FIG. 9d with electrical connection 99 and 10b, respectively) in the same manner for the deployment of stents. FIGS. 7a and 7b show thinned links 78. FIG. 9a shows thinned breakable links 94 in the planar structure 90 including cross-bands 96. FIGS. 8a and 8b show fragile plugs 88 to make its links breakable.

When a balloon 92 is inflated for expanding the planar structure 90 (FIG. 9c), torsional strain developed in the side beams 91 is effectively concentrated at the links 94 made in the beams 91 (FIG. 9a), leading to fracture (FIG. 9c). The resultant final shape can be helical by placing the links 94 at selected locations. This fracture is controlled breakage, and the fractured cross-section area is minimal.

In like fashion, torsional strain developed in side beams 101 (i.e., FIG. 10a) is effectively concentrated in breakable links 104 in the beams 101 leading to fracture as shown in FIG. 10b with electrical connection 109.

Experimental Results

The radial strength is a paramount mechanical characteristic in the stents. Several past efforts have assessed the strength in commercial stents [13,14]. To evaluate the devices of the present invention, short samples for involute and switchback designs were prepared and subjected to loading tests in which the reaction force per unit length of the stent is measured as a function of radial deformation. A sample is held in a groove mounted on the stage and compressed toward the probe. The gauge is rigidly fixed, and the displacement of the gauge probe is negligible compared to that of the sample. The force was measured by a gauge (Imada, Inc., IL, USA, DPS-1) that provides 1 mN resolution while first compressing the stent by 1.5 mm in 25 µm increments, and then while relaxing the deformation.

A commercial stent with 316 stainless steel of thickness varying over 90-130 µm was tested for comparison. Measurements demonstrate that the design that uses the involute cross-bands (design $1_A$) has the same radial strength to the commercial stent with similar diameter and twice the thickness. In addition, it exhibits better elastic recovery after loading, which suggested that it has better radial elasticity but the same stiffness as the commercial one. The switchback pattern (design 2), which as fewer cross-bands per unit longitudinal length, provides less radial strength than the involute pattern.

Figure 6:
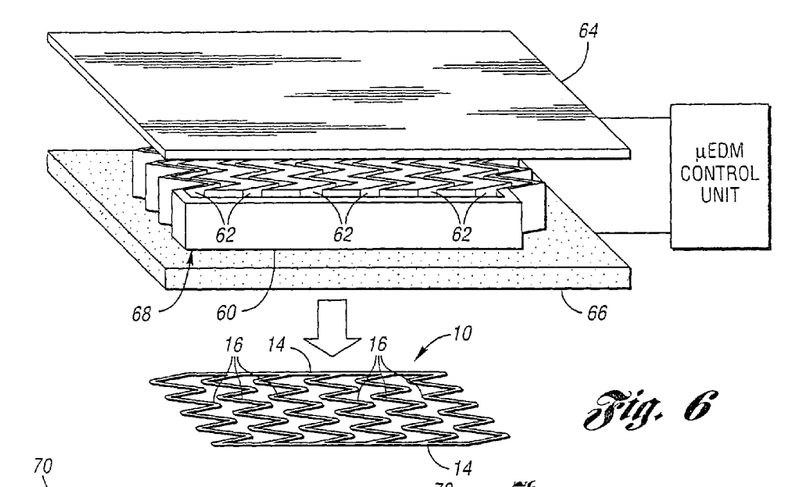

Orientation dependence of the radial strength was a concern since they were shaped from planar sheets as shown in FIG. 6. Identical samples with four cross-bands of design 2 were tested at two different orientations: (A) perpendicular to a plane that includes both side beams, and (B) parallel to the plane. The measurements demonstrate that the radial strength is similar in both cases.

The experimental results showed a few discontinuities in the response curve. As can be seen in FIG. 14, beams that correspond to $\dot{C}_n$ in FIG. 3 are designed to rotate about their center by −90° during the expansion. As a result, hinges $D_n$, and $B_{n+2}$ are positioned closely to each other. In addition, alternate cross-bands 26 in FIG. 3, which adjoin each other when they are mounted on the balloon 22, deform in a way that the gaps between their segments are reduced as the stent 20 expands since the side beams 24 are deformed to wave-like shapes. The combination of these effects results in increased probability of physical contact between the hinges $D_n$ and $B_{n+2}$ as the balloon 22 is being inflated. As loading is applied, hinges happen to come into contact and get intermeshed, and then snap apart as the loading is further increased. This particular sample, being design $1_A$, had a reduced gap of 50 µm between the cross-bands 26, which could also contribute to increase the probability. This undesirable mechanical interaction however can be improved by optimizing the layout.

Longitudinal compliance is a favored characteristic in stents. This is because the stent, fitted on an angioplasty balloon in a state that is only slightly expanded, must often travel a convoluted path along a blood vessel in order to reach the location of the deployment. In addition, longitudinal flexibility in a fully expanded stent can be beneficial for its deployment at curved sites. The longitudinal compliance of the fabricated stents was tested. A fully-expanded 7 mm long stent of design 1 was attached to a holder such that a 4 mm segment out of it was overhanging and unsupported. Using a force gauge, the displacement response was plotted for an end load. A similar test was also applied to the commercial stent tested before. The results reveal that the stent of the present invention had spring constants of 50 N/m and <5 N/m depending on the orientation, whereas that in the commercial stent resulted in 515 N/m. While this test was only performed on expanded stents, it suggests that the stents of the present invention perform favorably in this respect.

Figure 5:
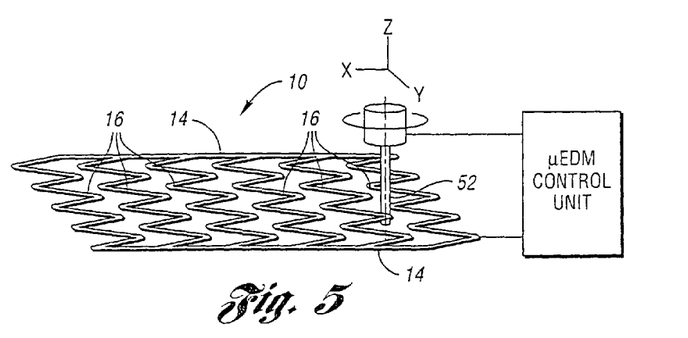

The design and fabrication of coronary artery stents of the present invention is preferably based on use of planar stainless steel foil and µEDM technology, as generally shown in U.S. Pat. No. 6,624,377. An electrode 52 is controlled by a control unit in FIG. 5. FIG. 6 shows a workpiece 64 processed by a device including a substrate 66 on which is formed a planar electrode, generally indicated at 68, having side and cross-band electrode members 60 and 62, respectively.

The devices are intended to be compatible with standard stenting tools and procedures. The wall patterns were designed using FEA so that both the stress relief and the mechanical strength are simultaneously achieved in the expansion. The devices include involute bands tied between a pair of side beams. Measurements demonstrate that the designs have the same radial strength as a commercial stent even though the former use metal that is only about half as thick. The thinner walls also contributed to achieving at least 10× higher longitudinal flexibility than a commercial one in the expanded state. Both the radial strength and the flexibility are found to have no significant dependence on orientation relative to the original planar direction of the foil. Dimensional variations in tubular diameter, longitudinal shrinkage, and radial recoiling in the expanded stents are at most a few percent.

All devices tested in this effort were fabricated by batch-compatible µEDM, which can open a path to exploit photolithography-based fabrication resources for the stent production [7]. As an extension of this technology for manufacturing stents, use of strategically-located breakable links as described above also facilitate fabrication of other 3-D structures such as antennas and transformers.

Figure 13A:
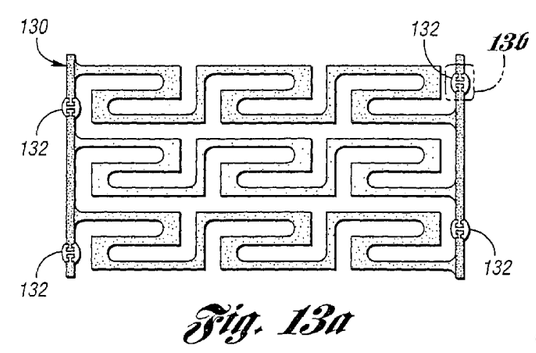
FIG. 13a is a top plan schematic view of another embodiment of a planar structure.
Figure 13B:
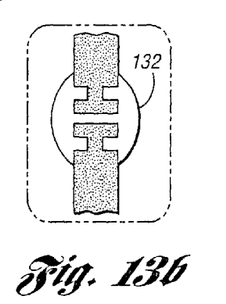

Furthermore, referring to FIGS. 13*a* and 13*b*, dielectric plugs 132 may be incorporated into a planar structure 130 to ensure that electric current does not attempt to flow in end rings in the expanded 3-D structure (not shown).

Figures 11A, 11B:
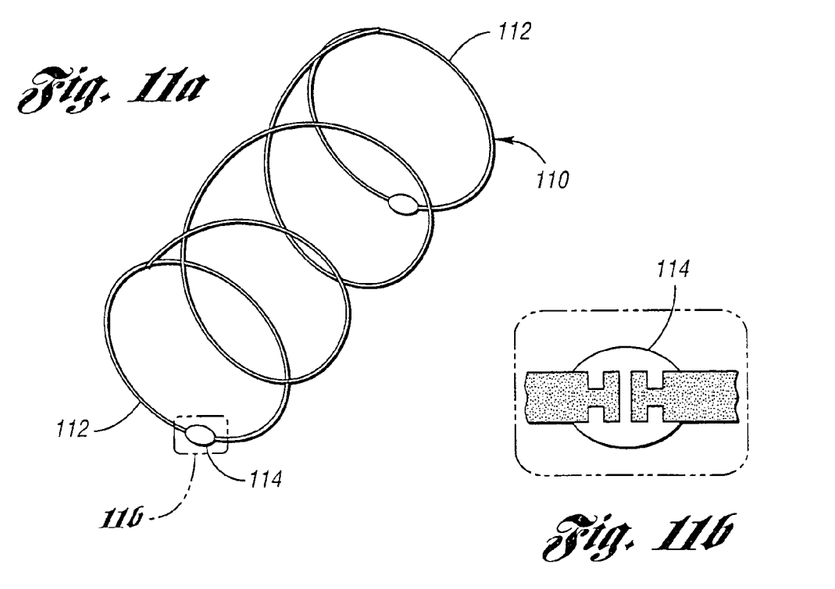

FIGS. 11*a* and 11*b* show an expanded 3-D structure in the form of a helical coil 110 having end rings 112 with such dielectric embedded plugs 114.

Figures 12A, 12B:
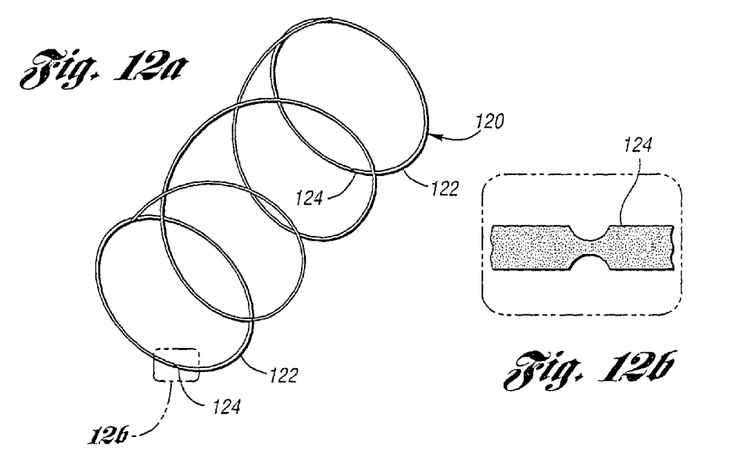

FIGS. 12*a* and 12*b* also show an expanded 3-D structure in the form of a helical coil 120 having end rings 122 with thinned portions 124 so that the end rings 122 are breakable to prevent current flow in the end rings 122.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus comprising:
   first and second spaced side beams which extend continuously along a longitudinal axis; and
   a plurality of spaced cross-bands which connect the side beams together, wherein the side beams and the cross-bands form an entirely planar structure in a first position, wherein a first set of the cross-bands are expandable in a first direction substantially perpendicular to the longitudinal axis to form a 3-D structure in a second position, and wherein the first and second side beams are on opposing, outer sides of the planar structure, and wherein said first and second spaced side beams are substantially straight in the first position,
   wherein the 3-D structure is a helical coil, and the helical coil includes first and second spaced rings at opposite ends thereof and wherein each of the rings is formed by an adjacent pair of expanded cross-bands,
   wherein at least the first ring includes a link portion having a mechanical strength lower than other portions of the first ring such that the first ring breaks at the link portion during expansion of the first set of cross-bands to erect the first ring and to open an electrical path formed by the first ring.

2. The apparatus as claimed in claim 1, wherein a second set of the cross-bands are expandable in a second direction substantially opposite the first-direction to form a mesh-like 3-D structure.

3. The apparatus as claimed in claim 2, wherein adjacent cross-bands are expandable in the opposite directions to form a mesh-like 3-D structure.

4. The apparatus as claimed in claim 1, wherein the planar structure plastically deforms during expansion so that the 3-D structure is free standing.

5. The apparatus as claimed in claim 2, wherein the planar structure plastically deforms during expansion so that the 3-D structure has a cylindrical geometry.

6. The apparatus as claimed in claim 2, wherein the 3-D structure is a tubular stent.

7. The apparatus as claimed in claim 1, wherein the planar structure includes a conductive foil.

8. The apparatus as claimed in claim 1, wherein each of the cross-bands includes a series of folded beams.

9. The apparatus as claimed in claim 8, wherein the folded beams have an involute pattern.

10. The apparatus as claimed in claim 8, wherein the folded beams have a switchback pattern.

11. The apparatus as claimed in claim 8, wherein each of the cross-bands includes hinges for interconnecting adjacent folded beams.

12. The apparatus as claimed in claim 1, wherein the side beams and cross-bands include biocompatible surface coatings.

13. The apparatus as claimed in claim 1, wherein the side beams and cross-bands are made of a biocompatible metal.

14. The apparatus as claimed in claim 1, wherein the cross-bands are made of a shape-memory alloy and wherein the planar structure is self-expandable.

15. The apparatus as claimed in claim 1, wherein the side beams and cross-bands are made of at least one of a biocompatible and a biodegradable polymer.

16. The apparatus as claimed in claim 1, wherein the side beams and cross-bands are formed by removing material from a sheet of material.

17. The apparatus as claimed in claim 16, wherein the sheet of material includes conductive foil and wherein side beams and cross-bands are formed by electric discharge machining the conductive foil.

18. The apparatus as claimed in claim 1, wherein at least the first side beam includes a link portion having a mechanical strength lower than other portions of the first side beam such that the first side beam breaks at the link portion during expansion of the first set of cross-bands.

19. The apparatus as claimed in claim 18, wherein the link portion is thinned relative to the other portions of the first side beam.

20. The apparatus as claimed in claim 18, wherein the link portion is made of a fragile material relative to the other portions of the first side beam.

21. The apparatus as claimed in claim 1, wherein the helical coil comprises at least one electrical inductor.

22. The apparatus as claimed in claim 1, wherein at least the first ring includes a dielectric part which mechanically connects but electrically insulates adjacent portions of the first ring.

23. The apparatus as claimed in claim 1, wherein at least one of the side beams and the cross-bands includes a dielectric part which mechanically connects but electrically insulates adjacent portions of the at least one of the side beams and the cross-bands, and wherein the dielectric part is in a coplanar orientation with the cross-bands and the side beams in the first position.

24. The apparatus of claim 1, wherein the first and second side beams extend the entire length of the planar structure.

25. A stent comprising:
first and second spaced side beams which extend along a longitudinal axis of the stent in the non-expanded position; and
a first set of cross-bands that connect the side beams together and a second set of cross-bands that connect the side beams together, wherein the side beams and the first set of cross-bands and the second set of cross-bands form an entirely planar structure in a non-expanded position where that planar structure is expandable into a 3-D structure in an expanded position,
wherein said first and second spaced side beams are substantially straight in the non-expanded position,
wherein the first set of cross-bands are expandable in a first direction substantially perpendicular to the longitudinal axis, where each cross-band in the first set includes a plurality of interconnected and folded back first and second beam sections in the non-expanded position, and
wherein the second set of cross-bands are expandable in a second direction substantially opposite the first-direction to form the 3-D structure along with the first set of cross-bands, where each of the cross-bands in the second set includes a plurality of interconnected and folded back first and second beam sections in the non-expanded position, wherein the first and second side beams are on opposing, outer sides of the planar structure,
wherein the 3-D structure is a helical coil, and the helical coil includes first and second spaced rings at opposite ends thereof and wherein each of the rings is formed by an adjacent pair of expanded cross-bands,
wherein at least the first ring includes a link portion having a mechanical strength lower than other portions of the first ring such that the first ring breaks at the link portion during expansion of the first set of cross-bands to erect the first ring and to open an electrical path formed by the first ring.

26. The stent as claimed in claim 25, wherein each of the plurality of interconnected and folded back first and second beam sections of the first set of cross-bands are interconnected by a hinge to open to expand the first set of cross-bands into the expanded position.

27. The stent as claimed in claim 26, wherein the first set of cross-bands includes six pairs of interconnected and folded back first and second beam sections that cooperate with one another to traverse the space between the side beams.

28. The stent as claimed in claim 26, wherein the first set of cross-bands have an involute pattern in which a longest beam section of the plurality of interconnected and folded back first and second beam sections extends perpendicular to the longitudinal axis.

29. The stent as claimed in claim 26, wherein the first set of cross-bands have a switchback pattern in which a longest beam section of the plurality of interconnected and folded back first and second beam sections extends parallel to the longitudinal axis.

30. The stent as claimed in claim 25, wherein the plurality of interconnected and folded back first and second beam sections of the first set of cross-bands rotate about a center by at least 90° during expansion into the expanded position.

31. The stent as claimed in claim 25, wherein the second set of cross-bands are identical to the first set of cross-bands when looking at the stent from a top plan view.

32. The stent as claimed in claim 25, wherein the second set of cross-bands are each offset from the first set of cross-bands when looking at the stent from a top plan view.

33. The stent as claimed in claim 25, wherein the second set of cross-bands are each 180° rotations of the first set of cross-bands when looking at the stent from a top plan view.

34. The stent as claimed in claim 25, wherein each of the first and second side beams includes a link that is breakable during expansion of the stent.

35. The stent of claim 25, wherein the first and second side beams extend the entire length of the planar structure.

36. A stent for use with a balloon catheter and comprising:
a unitary stent structure having a longitudinal axis;
the stent structure including first and second parallel spaced apart side beams extending parallel to the longitudinal axis;
a plurality of cross-bands extending across the stent structure and interconnecting the side beams, wherein the plurality of cross-bands and the side beams form the unitary stent structure into an entirely planar structure in a non-expanded position, wherein the first and second side beams are on opposing, outer sides of the planar structure and wherein said first and second spaced side beams are substantially straight in the first non-expanded position;
each of the cross-bands including a plurality of interconnected and folded back beam sections;
each of the cross-bands arranged to deflect away from a plane of the stent while in the non-expanded position to an expanded position in response to application of an expansion force from the balloon catheter;
a first set of the cross-beams arranged to deflect away from the plane in a first direction; and
a second set of the cross-beams arranged to deflect away from the plane in a second direction opposite the first direction,
wherein the stent structure in the expanded position includes first and second spaced rings at opposite ends thereof and wherein each of the rings is formed by an adjacent pair of expanded cross-bands,
wherein at least the first ring includes a link portion having a mechanical strength lower than other portions of the first ring such that the first ring breaks at the link portion during expansion of the first set of cross-bands to erect the first ring and to open an electrical path formed by the first ring.

37. The stent as claimed in claim 36, wherein each of the plurality of interconnected and folded back beam sections are interconnected by a hinge section, the hinge section arranged to permit the folded back beam sections to rotate relative to one another about a rotation axis.

* * * * *